(12) United States Patent
Obae et al.

(10) Patent No.: US 9,101,155 B2
(45) Date of Patent: Aug. 11, 2015

(54) FUNCTIONAL STARCH POWDER

(75) Inventors: Kazuhiro Obae, Nobeoka (JP); Ichirou Ibuki, Nobeoka (JP); Michihiro Sunago, Haibara (JP); Junichi Takahara, Kashiba (JP); Masaaki Endo, Nobeoka (JP)

(73) Assignees: ASAHI KASEI CHEMICALS CORPORATION, Tokyo (JP); SANWA CORNSTARCH CO., LTD., Nara (JP)

( * ) Notice: Subject to any disclaimer, the term of this patent is extended or adjusted under 35 U.S.C. 154(b) by 1661 days.

(21) Appl. No.: 10/564,151

(22) PCT Filed: Jul. 9, 2004

(86) PCT No.: PCT/JP2004/009841
§ 371 (c)(1),
(2), (4) Date: Jan. 11, 2006

(87) PCT Pub. No.: WO2005/005484
PCT Pub. Date: Jan. 20, 2005

(65) Prior Publication Data
US 2006/0204569 A1 Sep. 14, 2006

(30) Foreign Application Priority Data
Jul. 11, 2003 (JP) .................................. 2003-273176

(51) Int. Cl.
*A61K 47/36* (2006.01)
*A23L 1/0522* (2006.01)
*A23K 1/16* (2006.01)
*C08B 30/12* (2006.01)

(52) U.S. Cl.
CPC ............. *A23L 1/0522* (2013.01); *A23K 1/1643* (2013.01); *A61K 47/36* (2013.01); *C08B 30/12* (2013.01)

(58) Field of Classification Search
CPC ..... A23K 1/1643; A61K 47/36; A23L 1/0522
See application file for complete search history.

(56) References Cited

U.S. PATENT DOCUMENTS

| 4,755,397 | A |   | 7/1988  | Eden et al.     |         |
|-----------|---|---|---------|-----------------|---------|
| 5,362,329 | A | * | 11/1994 | Yoshino et al.  | 127/65  |
| 5,759,581 | A | * | 6/1998  | Baensch et al.  | 424/489 |
| 6,143,324 | A | * | 11/2000 | Michaud et al.  | 424/465 |
| 6,296,873 | B1|   | 10/2001 | Katzhendler et al. |     |
| 6,822,091 | B1| * | 11/2004 | Kesselmans et al. | 536/105 |
| 6,906,016 | B1| * | 6/2005  | Tsaur           | 510/130 |
| 2003/0018037 | A1 |  | 1/2003 | Lempriere et al. |      |

FOREIGN PATENT DOCUMENTS

| JP | 46-21471   | 6/1971  |   |
|----|------------|---------|---|
| JP | 48-68726   | 9/1973  |   |
| JP | 53-3725    | 2/1978  |   |
| JP | 56-11689   | 3/1981  |   |
| JP | 57-5700    | 1/1982  |   |
| JP | 58-32828   | 2/1983  |   |
| JP | 58-27774   | 6/1983  |   |
| JP | 59-47600   | 11/1984 |   |
| JP | 61-254602  | 11/1986 |   |
| JP | 62-7201    | 2/1987  |   |
| JP | 63-7531    | 2/1988  |   |
| JP | 4-130102   | 5/1992  |   |
| JP | 4-318001   | 11/1992 |   |
| JP | 6-100602   | 4/1994  |   |
| JP | 7-25902    | 1/1995  |   |
| JP | 7-508532   | 9/1995  |   |
| JP | 7-508533   | 9/1995  |   |
| JP | 8-143602   | 6/1996  |   |
| JP | 9-12426    | 1/1997  |   |
| JP | 10-195104  | 7/1998  |   |
| JP | 10-512873  | 12/1998 |   |
| JP | 2002-541090| 10/2000 |   |
| JP | 2001-514315| 9/2001  |   |
| JP | 2002-193792| 7/2002  |   |
| NL | WO00/40617 | * 7/2000|   |
| WO | WO 99/09066| 2/1999  |   |
| WO | 2004/010997| 2/2004  |   |
| WO | 2004/010998| 2/2004  |   |
| WO | 2004/011002| 2/2004  |   |

OTHER PUBLICATIONS

Supplementary European Search Report, mailed May 25, 2007 and issued in corresponding European Patent Application No. 04747309.5-1214.

* cited by examiner

*Primary Examiner* — Tigabu Kassa
(74) *Attorney, Agent, or Firm* — Staas & Halsey LLP

(57) ABSTRACT

Functional starch powder of 400% or more water retention capacity, 5 hr or more collapse time and 200 g or more gel indentation load. This functional starch powder is produced through the step of heating a starch raw material in the presence of water at 60 to 150° C. so as to swell starch particles of the starch raw material and the subsequent step of drying the thus swollen starch particles so as to obtain a powder mixture comprising starch particles and, lying in the exterior thereof, amylose and amylopectin.

3 Claims, 5 Drawing Sheets

FUNCTIONAL STARCH POWDER

This application is based on and hereby claims priority to PCT Application No. PCT/JP2004/009841 filed on Jul. 9, 2004 and Japanese Application No. 2003-273176 filed on Jul. 11, 2003, the contents of which are hereby incorporated by reference.

TECHNICAL FIELD

The present invention relates to functional starch powder, a composition including the functional starch powder and one or more active ingredients, and a method for producing the functional starch powder. More particularly, it relates to functional starch powder which permits control of the release of an active ingredient(s) when used in medicines, agrochemicals, fertilizers, feed, food, industry, cosmetics, etc. The composition containing the active ingredient(s) can be obtained as a sustained-release or rapid-release composition, depending on the amount of the functional starch powder incorporated into the composition.

BACKGROUND ART

For compositions having sustained-release properties, there are, for example, solid sustained-release medicines. The solid sustained-release medicines are very useful for controlling the blood level of the active ingredient(s), reducing the frequency at which the medicine must be taken; prolonging the effect of active ingredients that have a short half-life; and reducing the side effects of the active ingredients that have a narrow range between a minimum effective blood concentration and a side effect exhibition concentration. Regarding conventional solid sustained-release medicine, there are matrix type sustained-release tablets that use a hydrophilic polymer capable of forming a gel upon contact with water, and reservoir type sustained-release capsules that enclose granules of medicine. The granules within the capsules are formed by coating core particles with an active ingredient(s) and then coating the surface of the coated particles with a coating film capable of imparting sustained-release properties. Tablets are preferable to capsules and granules from the viewpoint of ease of taking, but reservoir sustained-release tablets have been disadvantageous in that when the sustained-release granules are compressed into the tablets, the coating film capable of imparting sustained-release properties is destroyed, so that the controlled release of the active ingredient(s) by dissolving becomes difficult.

On the other hand, patent document 1 and the like describe that hydrophilic polymers such as methyl cellulose (MC), hydroxypropyl cellulose (HPC) and hydroxypropylmethyl cellulose (HPMC) can be used as a release-sustaining base ingredient used in the matrix type sustained-release preparations. These hydrophilic polymers are advantageous, for example, in that they impart sustained-release properties by the formation of a complete gel layer by hydration in a solution having a low ionic strength, are hardly affected by pH, and are excellent in the stability of release by dissolution over a long period of time. They, however, have a problem, which is called dose dumping. If dose dumping occurs, it becomes impossible to hydrate the polymer in a solution having an intermediate or higher ionic strength, their gelation is suppressed, so that a large portion of the active ingredient(s) of a pharmaceutical preparation designed to have sustained-release properties is rapidly released, thus, the preparation exhibits no sustained-release properties. When the dose dumping occurs, the resulting rapid increase of the active ingredient(s) in the blood can induce death, depending on the efficacy of the active ingredient(s) that have a narrow range between the minimum blood level and the concentration where side effects are exhibited. Since the value of ionic strength in the gastrointestinal tract varies depending on regions of the tract and the food consumed, there has been a desire for a release-sustaining base ingredient which makes it possible to avoid the dose dumping in a wide ionic strength value range throughout the gastrointestinal tract.

Patent documents 2 to 5 describe simultaneous use of pregelatinized starch and a hydrophilic polymer such as hydroxypropyl cellulose or hydroxypropylmethyl cellulose as a means for avoiding the dose dumping. However, the pregelatinized starch (preferably drum-dried waxy corn starch) used in patent document 2 has no sustained-release effect in itself and is such that sustained-release properties are imparted by an ingredient other than the pregelatinized starch. In addition, the pregelatinized starch is disadvantageous in that the pregelatinized starch has only auxiliary effect on the release-sustaining base ingredient, because both the base ingredient and this auxiliary are necessary and the amounts added should be large, resulting in an increased size of a preparation. Patent documents 3 to 5 describe that the tablet tensile strength of pregelatinized starch at a solid fraction of 0.8 is 0.15 kN/cm$^2$. They, however, do not describe the upper limit of the tablet tensile strength. The tensile strength of the pregelatinized starch used in the comparative examples in these patent documents is 0.220 to 0.323 kN/cm$^2$, while the tensile strength of the functional starch powder of the invention is 0.7 to 1.5 kN/cm$^2$. Thus, they are clearly different. In patent documents 2 to 4, sustained-release properties are imparted by a combination of pregelatinized starch and hydroxypropylmethyl cellulose. These documents, however, neither describe nor suggest that starch having a tensile strength of 0.15 kN/cm$^2$ or more imparts sustained-release properties by itself. In addition, no starch having a tensile strength of more than 0.323 kN/cm$^2$ has been reported.

As starch used in the fields of medicines, agrochemicals, fertilizers, feed, food, industry, cosmetics, etc., there are pregelatinized starch, partly pregelatinized starch, crosslinked starch and the like. They are used as a disintegrating agent mainly in the medicine field.

All of the starches described in patent documents 6 to 15 rapidly collapse and do not impart any sustained-release properties. They are essentially different in the following respects from the starch of the invention, from which tablets that contain 60 to 100% of the starch powder are not disintegrated in 3 hours or more. That is, the modified starch of patent document 6 has a low degree of swelling of 2.5 to 12 and breadks down in 30 minutes. The tablets of patent document 7 that contain waxy starch disintegrate such that tablets containing 50% of the waxy starch are disintegrated within 60 seconds. The tablets of patent document 8 contain β-starch with an α-starch surface and tablets containing 17 to 30% of the β-starch are disintegrated within 2 minutes. The tablests of patent document 9 containing β-starch having 1 to 4% of α-starch adhered thereto disintegrate such that tablets containing 17 to 87% of this β-starch are disintegrated within 20 seconds. The starch of patent document 10, which is obtained by 5 to 20% pregelatinization of the surface of β-starch, breaks down within 2 minutes. The modified starch of patent document 11 has a cold-water-soluble matter content of 10 to 20%, and tablets containing 64 to 80% of this modified starch are disintegrated within 20 minutes. The processed starch of patent document 12 has a low degree of swelling of 3.0 to 6.0 and the tablets containing 10% of this processed starch are disintegrated within 6 minutes. The processed starch of patent document 13 has a cold-water soluble matter content of less than 10% by weight, a small swelling volume of 3 to 15 ml/g and a low water retention capacity of at most 610% and breaks down within 2 minutes. The starch of patent document 14 is a cross-linked starch powder having a low swelling property (swelling property in cold water: 3 to 25 ml) and breaks down more rapidly than Starch 1500 (Comparative Example 6). The processed starch of patent document 15 has a small swelling volume of 3 to 15 ml and is the starch represented by PCS (Comparative Example 5) and Starch 1500 (Comparative Example 6). Thus, these starches are essentially different from the starch of the invention.

Patent documents 16 to 20 describe a starch is used as a matrix base ingredient. Patent document 16 describes that matrix tablets are made of a high-molecular weight polysaccharide existing in nature. This document, however, describes only working examples relating to xanthan gum and no working example using starch and does not specifically describe starch capable of imparting sustained-release properties. Patent document 17 describes that a matrix agent substantially contains a crystalline straight-chain glucan and a glucan-degrading reagent. The straight-chain glucan, however, refers to amylose. The functional starch powder of the invention is different from the matrix agent because it contains amylopectin besides amylose as described hereinafter. In addition, in the case of the functional starch powder of the invention, the glucan-degrading reagent is not necessary for controlling the release of an active ingredient. Patent document 18 describes that a matrix raw material substantially contains a crystalline straight-chain glucan. This document, however, describes that amylopectin is removed from starch. The functional starch powder of the invention is different from the matrix raw material because it contains amylose and amylopectin.

Patent document 19 describes that the core tablets of film-coated tablets contain pregelatinized starch having an average degree of pregelatinization of 35 to 95%. Since the average degree of pregelatinization of the functional starch powder of the invention ranges from 40 to 98%, it is difficult to distinguish the starch of the invention from that of patent document 19 only by the average degree of pregelatinization. The functional starch powder of the invention, however, is clearly different from the latter, for example, in gel indentation load and the amount of swollen or dissolved amylose and amylopectin. The purpose of the starch of patent document 19 is to prevent the tablets from being impregnated with a liquid at the time of coating, and hence is obviously different from that of the functional starch powder of the invention. The coated tablets (the amount of the starch used: 14 wt %) themselves have excellent disintegrating properties. From these facts, it is clear that the starch of patent document 19 does not control the release of a drug. Patent document 20 describes spherical fine particles wholly or partly composed of a water-insoluble cottony polysaccharide. The fine particles of patent document 20 are produced, for example, by a biocatalyst process using starch synthase. On the other hand, the functional starch powder of the invention is produced only by heat treatment without using a catalyst such as an enzyme. Thus, the functional starch powder is obviously different from the fine particles of patent document 20. As to the shape of the functional starch powder of the invention, the functional starch powder comprises starch particles with a particle size of 50 to 100 μm having a structure formed by indenting a sphere or an oval in one or more parts thereof. Thus, the functional starch powder is clearly different from the fine particles of patent document 20, i.e., the spherical fine particles of 1 nm to 100 μm having a narrow particle size distribution. Patent document 21 describes starch particles obtained by drying an emulsion of an active ingredient and starch which has an amylopectin content of 65% or more and 80% by weight or more of which has a limited molecular weight of 10 to 10000 kDa. This starch, however, is water-soluble and the functional starch powder of the invention is different from the starch because it contains a water-insoluble component. Patent document 22 describes a method for making starch and a material into a slurry in a saturated aqueous salt solution and making the slurry into capsules, which includes blowing steam through starch at a pressure of at least 110 psi (0.78 MPa) in the presence of a salt to disperse the starch completely, heating the resulting starch slurry to a temperature of 120 to 180° C. at 55 to 120 psi (0.39 to 0.84 MPa) or more, and immediately exposing the slurry to atmospheric pressure to lower the temperature to 112° C. or lower. However, when the salt is present, amylose is precipitated, so that the product obtained by the method is not the starch particles according to the invention, i.e., starch particles with a particle size of 50 to 100 μm having an indentation in one or more parts thereof but a filmy and leaf-like product formed by the crystallization of amylose. Therefore, the product is different in shape from the fine particles according to the invention.

On the other hand, pregelatinized starch is used mainly in the food field as a thickening agent, feed for eel breeding or the like has been disadvantageous in that a gel formed by the starch is destroyed in the presence of α-amylase, resulting in a deteriorated release-sustaining capability, as reported in Chem. Pharm. Bull., 35(10)4346-4350(1987). It has been disadvantageous also in that at a high ionic strength, and it loses release-sustaining properties.

Patent document 1: U.S. Pat. No. 6,296,873
Patent document 2: JP-T-2002-541090
Patent document 3: WO200410997
Patent document 4: WO200410998
Patent document 5: WO200411002
Patent document 6: JP-B-46-21471
Patent document 7: JP-A-48-68726
Patent document 8: JP-B-53-3275
Patent document 9: JP-B-62-7201
Patent document 10: JP-B-58-27774
Patent document 11: JP-B-56-11689
Patent document 12: JP-A-58-32828
Patent document 13: JP-B-59-47600
Patent document 14: JP-B-63-7531
Patent document 15: JP-A-6-100602
Patent document 16: JP-T-10-512873
Patent document 17: JP-T-7-508532
Patent document 18: JP-T-7-508533
Patent document 19: JP-A-2002-193792
Patent document 20: JP-T-2001-514315
Patent document 21: US20030180371
Patent document 22: U.S. Pat. No. 4,755,397

DISCLOSURE OF THE INVENTION

Problem to be Solved by the Invention

The invention is directed to provide starch powder as a release-sustaining base ingredient used for controlling the concentration of an active ingredient(s) in medicines, agrochemicals, fertilizers, feed, food, industry, cosmetics, etc., which has a sufficient release-sustaining capability to constitute a sustained-release preparation mainly for medicinal use, assures pH stability and long-term stability, and is convenient. In addition, the invention is directed to providing a novel starch-based release-sustaining base ingredient that is not affected by ionic strength and is free from the dose dumping problem, so that it permits accurate control of an active ingredient(s), for example, throughout gastrointestinal tract.

Means for Solving the Problem

The inventors earnestly investigated the water retention properties, disintegration properties and gel characteristics of starch powder, and consequently found a starch powder which has all of sufficient release-sustaining capability, pH stability and long-term stability and does not cause the dose dumping because it is not affected by ionic strength, thereby the invention has been accomplished. That is, the invention is as follows.

(1) Functional starch powder having a water retention capacity of 400% or more, a collapse time of 5 hr or more and a gel indentation load of 200 g or more.

(2) Functional starch powder according to (1), wherein when the powder was dispersed in water, the amount of amylose and amylopectin, each of which is present in a swollen or dissolved state, ranges from 10 to 90% by weight.

(3) Functional starch powder according to (1) or (2), which includes starch particles with a particle size of 50 to 500 μm having an indentation in one or more parts thereof.

(4) A composition including functional starch powder according to any one of (1) to (3) and one or more active ingredients.

(5) A composition according to (4), wherein the one or more active ingredients are selected from pharmaceutically active ingredients, agrochemical ingredients, ingredients for fertilizer, ingredients for feed, ingredients for food, ingredients for cosmetic, coloring maters, flavoring materials, metals, ceramics, catalysts and surfactants.

(6) A composition according to (4) or (5), which controls the release of the active ingredient(s) so that the release may be sustained release or rapid release.

(7) A method for producing functional starch powder according to any one of (1) to (3), which includes heating a starch raw material in the presence of water at 60 to 150° C. to swell starch particles of the starch raw material and subsequently drying the swollen starch particles to obtain a powder mixture comprising starch particles and amylose and amylopectin which are present in the exteriors of these starch particles.

(8) A method for producing functional starch powder according to any one of (1) to (3), which includes heating a starch raw material in the presence of water at 60 to 150° C. to swell some or all of starch particles of the starch raw material at a volume ratio of 10 or more and subsequently drying the swollen starch particles to obtain a powder mixture comprising starch particles having a structure indented in one or more parts and amylose and amylopectin which are present in the exteriors of these starch particles.

(9) A method according to (7) or (8), wherein the starch raw material is that heat-treated at 100 to 130° C. under reduced pressure.

(10) A method according to (9), wherein the starch raw material is potato starch.

The term "function" in the term "functional starch powder of the present invention" means, for example, the increase of resistance to α-amylase, the enhancement of sustained-release capability (or rapid-release capability) for an active ingredient(s) in a composition produced from the functional starch powder and the active ingredient(s), the assurance of the sustained-release capability in a medium having a high ionic strength.

Advantages of the Invention

The invention is a novel starch powder which has satisfactory release-sustaining properties owing to its high α-amylase resistance that is not possessed by conventional natural or processed starch. The starch powder is excellent in pH stability and long-term stability and, moreover, is not affected by ionic strength, so that it is free from the dose dumping problem associated with conventional release-sustaining base ingredients and hence permits accurate control of an active ingredient(s).

BEST MODE FOR CARRYING OUT THE INVENTION

Figure 1:
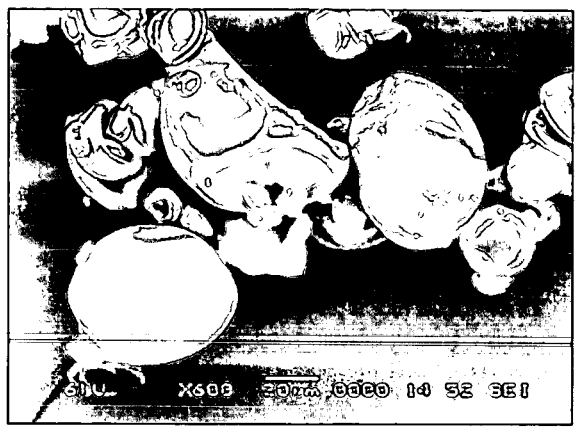
FIG. 1 An electron micrograph (600 magnifications) of starch powder B prepared in Example 2.

The invention is explained below in detail.

The functional starch powder of the invention should have a water retention capacity of 400% or more, more preferably 500% or more, particularly preferably 700%. The term "water retention capacity" is defined as the volume of pure water retained by starch after the centrifugation (2000G, 10 minutes) of a dispersion of 1 g of dry starch powder in pure water. When the water retention capacity is less than 400%, the starch powder is hydrated to form no gel, resulting in disintegration of tablets, or the starch powder cannot exhibit satisfactory release-sustaining properties because of rapid diffusion of an active ingredient(s) even when the starch powder forms a gel layer. The gel-forming capability is enhanced with an increase of the water retention capacity. When the water retention capacity is high, the gel is desirably not destroyed even at a high ionic strength, though the maximum water retention capacity is dependent on characteristics of a starch raw material and is at most 3000%.

In addition, the functional starch powder of the invention should have a collapse time of 5 hours or more. The term "collapse time" is defined as the disintegration time, in a test solution, of a cylindrical molded article with a diameter of 0.8 cm obtained by compressing 0.2 g of starch powder at 50 MPa. Here, the test solution is the second solution (pH 6.8) prescribed in the Japanese Pharmacopoeia, the 14th revision, p. 204 and a disintegration test is carried out by the use of an auxiliary plate according to the disintegration test method described in the Japanese Pharmacopoeia (14th revision). When the collapse time is less than 5 hours, no satisfactory release-sustaining properties can be attained. The upper limit of the collapse time depends on the desired degree of release-sustaining properties and is at most 240 hours.

Furthermore, the functional starch powder of the invention should have a gel indentation load of 200 g or more, preferably 300 g or more, particularly preferably 400 g or more. The term "gel indentation load" is defined as a maximum load applied when a cylindrical adapter is pressed for 3 mm at a rate of 0.1 mm/sec into a gel formed by immersing, in pure water for 4 hours, a cylindrical molded article with a diameter of 1.13 cm obtained by compressing 0.5 g of starch powder at 50 MPa. Here, the term "maximum load" means the following: when a layer of the gel is broken, the term means a load value at the time of the breaking; and when the gel layer is not broken, the term means a maximum load value which the adapter applies before it intrudes for 5 mm into the gelatinized cylindrical molded article. When the gel indentation load is less than 200 g, the diffusion of an active ingredient(s) in a gel layer formed by the starch powder becomes rapid, so that no satisfactory release-sustaining properties are exhibited. Although the gel indentation load is preferably high because the release-sustaining capability of the starch powder is enhanced with an increase of the gel indentation load, it is at most about 3000 g.

As to the shape of starch particles constituting the functional starch powder of the invention, the starch particles have more preferable characteristic in that they have a structure formed by indenting a sphere or an oval in one or more parts thereof. As to the particle size of the starch particles constituting the functional starch powder of the invention, the functional starch powder preferably includes starch particles having a particle size in the range of 50 to 500 μm, preferably 50 to 300 μm, more preferably 50 to 100 μm, when observed by SEM (scanning electron microscope) at a magnification of 200 to 1500. As to the content of such starch particles having a structure formed by indenting a sphere or an oval in one or more parts thereof, the functional starch powder preferably contains such starch particles so that for example, when it is observed at a modification of 600, the proportion (% by the number of particles) of such starch particles to all particles observable in the field of vision may be 5% or more, preferably 10% or more. The content (% by the number of particles) measured by such observation is considered as the content (% by weight) based on the weight of all the starch particles. When particle size of the starch particles having an indentation in one or more parts thereof is less than 50 μm, the starch particles hardly release, outside them, amylose and amylopectin which can be swollen or dissolved in a sufficient volume of water, and hence no sufficient sustained-release properties can be imparted. This is not desirable. When the functional starch powder is dispersed in water, the amount of amylose and amylopectin, each of which is present in a swollen or dissolved state, is preferably in the range of 10 to 90% by weight based on the weight of all the starch particles. When the particle size of the starch particles having an indentation in one or more parts thereof is more than 500 μm, the amount of amylose and amylopectin, which are present in the exterior of starch particles, exceeds 90% by weight based on the weight of all the starch particles and hence the resistance to α-amylase is decreased, so that no satisfactory sustained-release properties can be imparted. This is not desirable.

The starch particles constituting the functional starch powder of the invention have a structure formed by indenting a sphere or an oval in one or more parts thereof, have a particle size of 50 to 500 μm, and may be an aggregate having particles of 1 to 50 μm having a structure formed by indenting a sphere or an oval in one or more parts thereof, as particles adhered to a part of the exterior of the aggregate.

The starch particles constituting the functional starch powder of the invention are preferably non-crystalline. The starch particles can be judged to be crystalline or non-crystalline by a polarization image (magnification: 10) under an optical microscope. When the starch particles are crystalline, a light polarization image (for example, an image called "crisscross observed by polarization microscope" in the case of raw starch) appears.

The bulk density of the functional starch powder of the invention is preferably in the range of 0.1 to 0.70 g/cm$^3$, more preferably 0.15 to 0.70 g/cm$^3$, and most preferably 0.20 to 0.70 g/cm$^3$. When the bulk density is less than 0.1 g/cm$^3$, the fluidity is low, so that segregation by weight is undesirably caused when a composition comprising the functional starch powder and an active ingredient(s) is tablets. On the other hand, when the bulk density is more than 0.70 g/cm$^3$, the moldability of the composition is deteriorated, so that a suitable practical hardness is undesirably unattainable. The viscosity of the functional starch powder of the invention is preferably 1000 mPa·s or less, more preferably 500 mPa·s or less, and most preferably 400 mPa·s or less, in an aqueous solution of 2% concentration at 25° C. When the viscosity is more than 1000 mPa·s, handling of the functional starch powder undesirably becomes troublesome when the functional starch powder is added in the form of an aqueous solution. The lower limit of the viscosity is preferably as close to the viscosity of water of 1 mPa·s as possible.

A method for producing the functional starch powder of the invention is described below.

The functional starch powder of the invention is produced through a step of heating a starch raw material in the presence of water at 60 to 150° C. to swell some or all of starch particles of the starch raw material and a step of drying the resulting swollen starch particles to obtain a powder mixture including starch particles with an indentation in one or more parts and amylose and amylopectin which are present in the exteriors of these starch particles.

The starch raw material referred to herein is not particularly limited so long as it contains a starch material such as natural starch, aged starch or crosslinked starch of rice, glutinous rice, corn, waxy corn, amiro corn, sorghum, wheat, barley, taro, green gram, potato, lily, dogtooth violet, tulip, canna, pea, shiwa pea, chestnut, arrowroot, yam, sweet potato, broad bean, snap bean, sago, tapioca (cassava), bracken, lotus, water caltrop or the like. Potato is preferred because its starch particles have a high swelling property, so that the water retention capacity can easily be controlled to be high.

A material obtained by subjecting a starch raw material to wet heat treatment such as heat treatment at 100 to 130° C. under reduced pressure is discussed in JP-A-4-130102 or JP-A-7-25902 and is preferred because when such a material is used, the gelatinization initiation temperature is raised, so that the swelling properties of particles are enhanced. That is, JP-A-4-130102 discusses (1) a method in which starch is placed in a sealable container resistant to both internal and external pressures and having both a pressure-reducing line and a pressurized steam line attached, and the pressure is reduced, followed by application of pressure and heat by steam introduction, or the above procedure is repeated, whereby the starch is heated for a predetermined time, and then the heated starch is cooled. JP-A-4-130102 discusses (2) a method according to (1), wherein by adjusting the temperature in a can to at least 120° C., starch having a very high α-amylase adsorption capability is produced, which is that when an aqueous suspension of the starch is heated, it has substantially no viscosity though starch particles expand. JP-A-4-130102 describes a method according to (1) and (2), wherein cooling is conducted under reduced pressure after the heating. JP-A-7-25902 discusses, for example, (1) a method for producing wet-heat-treated starch grains obtained by wet heat treatment of starch grains, which includes repeating at least once a first step of subjecting starch grains charged into a pressure container to pressure reduction and a second step of introducing steam into the container to conduct heating and pressurizing, after the pressure reduction; and (2) a production method according to (1), wherein in the above second step, the heating is conducted at 80° C. or higher for 5 minutes to 5 hours. Thus, the wet-heat-treated starch is composed of particles each of which has a hollow interior and a shell having an increased crystallinity. It is characterized in that a polarization crisscross pattern observed as a polarization image under an optical microscope is vaguer than that observed in the case of raw starch, namely, non-birefringent particles are decreased. The hollow portion seems to have a structure formed by the loosening of the crystalline states of amylose and amylopectin, and the treated starch is characterized in that its digestibility with α-amylase is higher than that of raw starch. The viscosity of an emulsion of the wet-heat-treated starch adjusted to 5% concentration is preferably 400 Brabender units (BU) or less during heating from 50° C. to 95° C., and the maximum viscosity of the emulsion is preferably 1000 BU or less when the emulsion is maintained at 95° C. for 30 minutes. As the starch raw material, one or a mixture of two or more of the above-exemplified materials may be freely used. The size of particles of the starch raw material is preferably as large as possible from the viewpoint of ease of expanding.

The term "in the presence of water" used herein with respect to the starch raw material means a state in which the starch raw material and water are present and the water content is 40% by weight or more. A method for heating in the invention is not particularly limited so long as it is a well-known method. As the method, one embodiment is a method of placing the starch raw material in the presence of water in a jacketed reactor and introducing steam into the reactor to heat the starch raw material; a method of mixing the starch raw material in the presence of water with steam; a method of heating the starch raw material in the reservoir of a drum dryer; and a method of carrying out gelatinization and spraying at the same time during spray drying while supplying steam to a starch slurry. The method of mixing the starch raw material in the presence of water with steam is preferable because it facilitates the assurance of time for heating starch particles. The heating temperature is any temperature so long as the temperature of a liquid obtained by the gelatinization of starch by the above methods is 60 to 150° C., preferably 90 to 140° C., more preferably 90 to 130° C., and most preferably 100 to 120° C.

The functional starch powder of the invention should be produced by heating the starch raw material in the presence of water at 60 to 150° C. to swell some or all of starch particles of the starch raw material at a volume ratio of 10 or more. The term "volume ratio" is defined as $[b/a]^3$ when the average particle sizes before and after the swelling are taken as a (μm) and b (μm), respectively. The average particle size referred to here is calculated by summing up the maximum diameters m (μm) of individual particles observed under an optical microscope (magnification: 10, OPTIPHOT-POL mfd. by Nikon) and dividing the sum by the number (n) of particles subjected to the measurement (Σm/n). When starch particles constituting the starch raw material is heated in the presence of water, they expand near a gelatinization initiation temperature intrinsic to the starch particles. During the swelling, in the starch particles of the starch raw material, the hydrogen bonds of amylose and amylopectin, which constitute the shells of the starch particles, are destroyed by the heating, and water intrudes into the interiors of the starch particles, so that amylose and amylopectin in the interiors of the particles are decreased in molecular weight by heat to be released to the exteriors of the starch particles. The ratio between amylose and amylopectin is intrinsic to the kind of the starch raw material (the amylose content of potato starch is about 25%). The ratio between amylose and amylopectin is not changed even after they are released to the exteriors of the starch particles. It is inferred that the molecular weight distribution is shifted to a low molecular weight side.

Whether or not amylose and amylopectin, which constitute the interiors of the particles, have been released to the exteriors of the particles during the expansion can be confirmed by a photomicrograph (magnification: 20 to 30) by adding several drops of a 1/50 to 1/200 normality iodine solution to a suspension of starch subjected to the swelling treatment by heating. In the field of vision of the photomicrograph, portions stained blue other than the starch particles are amylose and amylopectin released from the interiors of the particles. When the starch particles expand and then dried, a mixture of starch particles and amylose and amylopectin released to the exteriors of the particles from the interiors is dried to become powder. When the amount of expanded or dissolved amylose and amylopectin defined herein is measured in the resulting dry powder, it can be confirmed that the amount of amylose and amylopectin released to the exteriors of the starch particles ranges from 10 to 90% by weight.

When the swelling of the starch particles is insufficient, the volume ratio in the swelling cannot be 10 or more and the amount of amylose and amylopectin released to the exteriors of the starch particles becomes less than 10%, so that no satisfactory release-sustaining properties can be exhibited. This is not desirable. In addition, unless such starch particles are added in a large amount of more than 10% like partly pregelatinized starch, it becomes difficult to bind an active ingredient(s) to other additives, which is not desirable. An example of such starch particles is partly pregelatinized starch such as the starch particles of Comparative Example 5. As to the shape of such starch particles after drying, indented particles having a particle size of less than 50 μm are observed in only a small amount, and most of the starch particles become an aggregate in which indented particles of less than 50 μm are aggregated to such an extent that the boundary surfaces among constituent particles are not clear. Such an aggregate has a size of 50 to 100 μm but is utterly different from the functional starch particles of the invention because its particles cannot be distinguished from one another as individual particles having clear boundary surfaces among them.

The upper limit of the volume ratio in the swelling is at most 400, preferably 100, though it varies depending on the starch raw material. When the volume ratio is more than 400, amylose and amylopectin, which form the shell structure of starch, are also expanded to be dispersed as molecules and are gradually dissolved and released to the exteriors of starch particles, so that the starch particles themselves disappear. Therefore, the amount of amylose and amylopectin, which are present in the exteriors of the particles, exceeds 90% based on the total amount of the starch particles, so that no sufficient gel strength is attained, and moreover, the resistance to α-amylase is lost, so that no sufficient release-sustaining capability is exhibited. This is not desirable. When the starch particles become unable to retain the shape of their shell structures and substantially all of them become amylose and amylopectin that can expand or dissolved in water, they become flaky or massive crystalline particles (showing a polarization image in a photomicrograph) after drying, for example, because swollen or dissolved amylose and amylopectin become β-amylose and β-amylopectin. Such particles are clearly different from starch particles constituting the functional starch powder of the invention.

In the case of the functional starch powder of the invention, starch particles are swollen by a volume ratio of 10 or more by heating, so that the particle size of the swollen starch particles after drying is 50 to 500 μm. Although a method for drying is not particularly limited, it includes, for example, freeze-drying, spray drying, drum drying, tray drying, air-drying, vacuum drying, and drying by solvent replacement. Industrially, spray drying and drum drying are preferred. The solid content of a liquid at the time of the drying is approximately 0.5% to 60%. When the solid content is less than 0.5%, the productivity is undesirably deteriorated. When the solid content is 60% or more, the viscosity becomes high, so that the yield is undesirably decreased. The solid content is preferably 1 to 30%, more preferably 1 to 20%.

When 1 g of the functional starch powder of the invention is dispersed in 100 cm$^3$ of pure water and stands for 16 hours, the lower layer portion of the dispersion separated into upper and lower layers is observed under an optical microscope (magnification: 10), it is preferable that the shell structure inherent in a starch raw material for the functional starch powder is completely present without loss thereof. The functional starch powder of the invention is essentially different from a starch where nothing is observed in the above-mentioned lower layer portion, or a starch which has a flaky, massive or the shell-like structure formed by the conversion of swollen or dissolved amylose and amylopectin to β-amylose and β-amylopectin in the lower layer portion.

For imparting release-sustaining properties, resistance to α-amylase and resistance to ionic strength, the amount of amylose and amylopectin, each of which is present in a swollen or dissolved state, should be in a definite range. The term "swollen or dissolved amylose and amylopectin" means amylose and amylopectin expanded or dissolved by heating of a starch raw material in the presence of water that are so transparent or semitransparent that their shapes cannot be observed under an optical microscope. Their amount (% by weight) can be determined by dispersing 1 g of starch powder in 100 cm$^3$ of pure water, allowing the resulting dispersion to stand for 16 hours and calculating the amount from the volume of the upper layer portion of the dispersion separated into upper and lower layers and the weight of solids in 30 cm$^3$ of the upper layer (the volume (cm$^3$) of the upper layer portion÷30×the weight (g/cm$^3$) of solids in 30 cm$^3$ of the upper layer÷ the dry weight (g) of 1 g of the starch×100). The amount in the case of the starch powder of the invention ranges from 10 to 90% by weight. When the amount is less than 10% by weight, the water retention is insufficient, so that no release-sustaining properties are exhibited. This is not desirable. When the amount is more than 90% by weight, the water retention is lowered, so that the resistance to α-amylase, release-sustaining capability and resistance to ionic strength are undesirably deteriorated.

When the amount of swollen or dissolved amylose and amylopectin is controlled to be within the above range, the shell structures of starch particles are not completely lost and can be clearly observed in the lower layer portion in the above-mentioned measurement. The term "degree of swelling" is defined as the volume of the lower layer portion of a dispersion separated into upper and lower layers which is obtained by dispersing 1 g of starch powder in 100 cm$^3$ of pure water, followed by standing for 16 hours. The degree of swelling of the functional starch powder of the invention is approximately 0.5 cm$^3$ to 60 cm$^3$ and is preferably 10 cm$^3$ to 50 cm$^3$.

Pregelatinized starch and partly pregelatinized starch, which are used mainly in medicines, are obtained by gelatinizing natural starch by heating and then drying the gelatinized starch. As described in JP-B-59-47600, starch with excellent disintegrating properties can be obtained with starch mostly composed of particles with a shell structure and inhibited as much as possible from releasing swollen amylose and amylopectin by dissolution by heating at a temperature, which is above 50° C. and below a temperature about 10° C. higher than an intrinsic gelatinization initiation temperature (which is a temperature lower than 90° C. though depending on the kind of starch). However, although such starch includes particles with a shell structure, the particle size of a single swollen particle in the starch is less than 50 μm and sufficient water retention is impossible because of the insufficient swelling in water, or because of the amount of swollen amylose and amylopectin is insufficient which results in an insufficient gel indentation load. Therefore, such starch does not exhibit release-sustaining properties.

Pregelatinized starch used mainly in food is produced by a method such as drum drying at about 150° C. or extrusion with an extruder at 120 to 160° C. under high pressure. In pregelatinized starch obtained by such a method, its particles are excessively swollen because of too high a gelatinization temperature, almost no particles having a shell structure are present, and its particles have a flaky or massive shape different from a shell structure inherent in starch particles, which is the same as a flaky, massive or the like structure formed by the conversion of swollen amylose and amylopectin to β-amylose and β-amylopectin. That is, in conventional pregelatinized starch, swollen or dissolved amylose and amylopectin and flaky or massive particles formed by the conversion to β-amylose and β-amylopectin are present at the same time, and only the flaky or massive particles have a visually confirmable shape. Starch particles composed mainly of amylose and amylopectin swollen with loss of the shell structures by such excessive gelatinization are not desirable because they have a low gel indentation load and a low resistance to α-amylase and do not exhibit release-sustaining capability and resistance to ionic strength.

That is, the functional starch powder of the invention is produced by heating a starch raw material at 60 to 150° C. to swell starch particles at a volume ratio of 10 or more and then drying the swollen starch particles to obtain a powder mixture including starch particles and, lying in the exterior thereof, amylose and amylopectin. Surprisingly, the functional starch powder obtained by such a production process has a high resistance to α-amylase, a high resistance to ionic strength and a sufficient release-sustaining capability, which are not possessed by conventional pregelatinized starch and partly pregelatinized starch.

The composition of the invention including the functional starch powder and one or more active ingredients can be used for controlling the concentration of the active ingredient(s) in the fields of medicines, agrochemicals, fertilizers, feed, food, industry, cosmetics, etc. The amount of the starch powder of the invention incorporated into the composition is approximately 0.1 to 99.99% by weight. When the amount is less than 0.1% by weight, the concentrate of the starch powder of the invention is not controlled. When the amount is more than 99.99% by weight, a sufficient amount of the active ingredient(s) cannot be added, so that the therapeutic effect, efficacy and the like of the active ingredient(s) cannot be expected. The starch powder of the invention is usually used in the range of 0.5 to 95% by weight, preferably about 0.5 to about 90% by weight.

The active ingredient(s) referred to herein includes the following, but is not limited to: pharmaceutically active ingredients, agrochemical ingredients, ingredients for fertilizer, ingredients for feed, ingredients for food, ingredients for cosmetic, coloring maters, flavoring materials, metals, ceramics, catalysts, surfactants and the like. The active ingredient(s) may be in the form of any of powder, crystals, oil, a liquid, a semisolid and the like. The shape may be any of powder, fine granules, granules and the like. The active ingredient(s) may be coated to control the rate of dissolution, to reduce bitterness, or the like. The above-exemplified active ingredients may be used alone or in combination. As the active ingredient(s), the pharmaceutically active ingredients are the most preferable.

For example, for the pharmaceutically active ingredients orally administrable drugs such as antipyretic analgesic antiphlogistics, hypnotic sedatives, sleepiness inhibitors, dinics, infant analgesics, stomachics, antacids, digestives, cardiotonics, drugs for arrhythmia, hypotensive drugs, vasodilators, diuretics, antiulcer drugs, drugs for controlling intestinal function, therapeutic drugs for osteoporosis, antitussive expectorants, antasthmatics, antibacterials, drugs for pollakiuria, tonics, vitamin preparations, and the like can be used. These active ingredients may freely be used alone or in combination.

One of the functions of the functional starch powder of the invention is its ability to control the release of the active ingredient(s) in the composition including the functional starch powder and the active ingredient(s). Here, the phrase "control the release of the active ingredient(s)" means controlling the release so that the amount of the active ingredient(s) released by the composition in a liquid medium may be in a definite range at intervals of a definite time; or releasing the whole of the active ingredient(s) within a definite time. The phrase "controlling the release so that the amount of the active ingredient(s) may be in a definite range at intervals of a definite time" means that for example, when the whole of the active ingredient(s) is released in 10 to 12 hours, the release is controlled so that the rate of release by dissolution measured according to the release-by-dissolution test method, which is the second method (paddle method) described in the Japanese Pharmacopoeia (14th revision) may be 20 to 40% after 1 hour, 40 to 60% after 5 hours, and 70% or more after 7 hours. In addition, when the whole of the active ingredient(s) is released in a long time such as 12 to 240 hours, it is also possible to control the release by properly lengthening the intervals of 1, 5 and 7 hours. The phrase "releasing the whole of the active ingredient(s) within a definite time" means that the whole of the active ingredient(s) is released in a short time such as 30 minutes. Here, although the term "the whole" means the whole of the theoretical amount of the active ingredient(s) added, the release is considered as the release of the whole when the amount of the active ingredient(s) released is in the range of 95 to 105%, inclusive of analysis errors.

In the case of the functional starch powder of the invention, there are two possible, seemingly different, ways to control the rate of dissolution, as described above. By these ways of controlling the release by dissolution, the so-called sustained-release effect, an effect of controlling the release so that the amount of the active ingredient(s) released may be in a definite range at intervals of a definite time, can be obtained (in other words, a sustained-release composition containing the functional starch powder of the present invention can be obtained) by incorporating the functional starch powder into the composition in an amount of, for example, approximately 10 to 95% by weight based on the weight of the composition. In addition, the so-called rapid-release effect, an effect of releasing the whole of the active ingredient(s) within a definite time can be obtained (in other words, a rapid-release composition containing the functional starch powder of the present invention can be obtained) by incorporating the functional starch powder into the composition in an amount of, for example, approximately 0.1 to 5% by weight based on the weight of the composition.

The active ingredient(s) and optionally other additives can be granulated by a well-known wet granulation method such as high-speed stirring granulation, extrusion granulation or fluidized-bed granulation. In this case, when the functional starch of the invention is used in the composition in an amount of approximately 0.1 to 10% by weight, preferably approximately 0.1 to 5% by weight, based on the total weight of the composition, the amount of amylose and amylopectin, each of which is in a swollen or dissolved state, is in a specified range, so that it becomes possible to bind the active ingredient(s) and optionally other additives to the functional starch. Moreover, granules having an average particle size in the range of 50 to 500 μm can be obtained. Furthermore, a sufficient hardness can be imparted to a composition obtained by compression-molding the obtained granules by a well-known method. When a comparison is made at the same adding amount, the functional starch powder of the present invention can impart a higher hardness than do cellulose derivatives such as hydroxypropyl cellulose. The functional starch powder of the invention gives a sharp particle size distribution when used either in the form of powder or in the form of a suspension, solution or semi-solution in a medium such as water. For obtaining granules having a sharper particle size distribution, the functional starch powder is preferably used in the form of powder.

In addition, the functional starch powder is advantageous in that it includes starch particles with a particle size of 50 to 500 μm having a structure formed by indenting a sphere or an oval in one or more parts thereof, so that when the granules are compressed into tablets, the disintegration time of the tablets having a practical hardness of 40N or more can be reduced because the starch particles are swollen in water. In the case of a conventional binder such as a cellulose derivative (e.g. hydroxypropyl cellulose), when its amount is increased, coarse particles are formed, so that the average diameter of granules is increased. As a result, the disintegration of tablets obtained by compressing such granules is slowed. Therefore, the diameter of granules should be set at a suitable diameter. The functional starch powder of the invention is advantageous in that even when its adding amount is increased, it can be granulated without remarkable increase of the average diameter of granules, so that the disintegration of tablets obtained by compressing such granules is not slowed. Most of pregelatinized starches in use as a binder are completely gelatinized starches and do not include starch particles with a particle size of 50 to 500 μm having a structure formed by indenting a sphere or an oval in one or more parts according to the inventon. Therefore, they have been disadvantageous in that the disintegration of tablets obtained by compressing granules is slow. They have been disadvantageous particularly in that the disintegration is slowed with the lapse of time because they contain a large amount of gelatinized amylose and amylopectin.

If necessary, the composition of the invention may contain other components such as disintegrating agents, binders, fluidizing agents, lubricants, correctives, flavoring materials, coloring matters, sweeteners, etc. besides the active ingredient(s) and the functional starch powder. The other components may be used as a diluent.

The binders are not particularly limited and include, for example, sugars such as sucrose, glucose, lactose, fructose, trehalose, etc.; sugar alcohols such as mannitol, xylitol, maltitol, erythritol, sorbitol, etc; water-soluble polysaccharides such as gelatin, pullulan, carrageenan, locust bean gum, agar, konjak mannan, xanthan gum, tamarind gum, pectin, sodium alginate, gum arabic, etc.; celluloses such as crystalline celluloses (e.g. "Avicel" PH-101, PH-101D, PH-101L, PH-102, PH-301, PH-301Z, PH-302, PH-F20, PH-M06, M15, M25, "Ceolus" KG-801 and KG-802, manufactured by Asahi Kasei Corp.), powdered cellulose, hydroxypropyl cellulose, methyl cellulose, etc.; starches such as pregelatinized starch, starch paste, etc.; synthetic polymers such as poly(vinylpyrrolidone)s, carboxyvinyl polymers, poly(vinyl alcohol)s, etc.; and inorganic compounds such as calcium hydrogenphosphate, calcium carbonate, synthetic hydrotalcite, magnesium aluminate silicate, etc. These binders may be used alone or in combination.

The crystalline celluloses usable as the binder are preferably those having an excellent compactibility. Use of the crystalline cellulose having an excellent compactibility permits compression into tablets at a low striking pressure. Therefore, granule-containing tablets can be obtained which permit retention of the activity of an active ingredient(s) that is inactivated by striking pressure. Moreover, a high hardness can be imparted by adding a small amount of such crystalline cellulose, and hence, a bulky active ingredient(s) or a drug containing various kinds of active ingredients can be made into tablets. Such crystalline cellulose is advantageous, for example, in that in some cases, it permits reduction of the size of tablets, is excellent in ability to support a liquid component and can suppress hindrances in compression into tablets.

The disintegrating agents are not particularly limited and include, for example, celluloses such as sodium croscarmellose, carmellose, calcium carmellose, sodium carmellose, low-substituted hydroxypropyl cellulose, etc.; starches such as sodium carboxymethyl starch, hydroxypropyl starch, rice starch, wheat starch, corn starch, potato starch, partly pregelatinized starch, etc.; celluloses such as crystalline cellulose, powdered cellulose, etc.; and synthetic polymers such as crospovidone, crospovidone copolymers, etc. These disintegrating agents may be used alone or in combination.

The fluidizing agents are not particularly limited and include silicon compounds such as hydrated silicon dioxide, light silicic anhydride, etc. These fluidizing agents may be used alone or in combination.

The lubricants are not particularly limited and include magnesium stearate, calcium stearate, stearic acid, sucrose fatty acid esters, talc, etc. These lubricants may be used alone or in combination.

The correctives are not particularly limited and include glutamic acid, fumaric acid, succinic acid, citric acid, sodium citrate, tartaric acid, malic acid, ascorbic acid, sodium chloride, 1-menthol, etc. These correctives may be used alone or in combination.

The flavoring materials are not particularly limited and include orange, vanilla, strawberry, yogurt, menthol, oils (e.g. fennel oil, cinnamon oil, orange-peel oil and peppermint oil), green tea powder, etc. These flavoring materials may be used alone or in combination.

The coloring matters are not particularly limited and include food colors (e.g. food red No. 3, food yellow No. 5 and food blue No. 11), copper chlorophyllin sodium, titanium oxide, riboflavin, etc. These coloring maters may be used alone or in combination.

The sweeteners are not particularly limited and include aspartame, saccharin, glycyrrhizic acid dipotassium salt, stevia, maltose, maltitol, thick malt syrup, powdered sweet hydrangea, etc. These sweeteners may be used alone or in combination.

When the composition is used as a medicine, the composition includes, for example, solid pharmaceutical preparations such as tablets, powders, fine granules, granules, extracts and pills. They can be produced by well-known methods such as extrusion granulation, crushing granulation, fluidized-layer granulation, high-speed stirring granulation, tumbling flow granulation and the like. The composition may be utilized not only as medicines but also as foods (e.g. confectionery, health food, texture improvers and dietary fiber supplements), solid foundations, bath agents, animal drugs, diagnostic drugs, agrochemicals, fertilizers, ceramic catalysts and the like.

As an example of the composition, tablets are preferably prepared from the viewpoint of productivity, the ease of administration/ingestion and the ease of handling. The tablets are obtained by a direct tableting method, dry granule compression method, wet granule compression method, wet granule compression (extragranular addition of MCC) or the like. Although the tablets may be multi-core tablets containing, as inner cores, tablets previously obtained by compression molding, they are preferably, in particular, tablets obtained by direct tabletting, from the viewpoint of cost and ease.

The composition of the invention makes it possible to impart sustained-release properties to pharmaceutical preparations by a simple method including mixing one or more active ingredients with the functional starch powder of the invention and formulating the mixture into tablets, a powder, granules, fine granules or the like using a known method. Therefore, troublesome operations such as coating of granules or tablets with a coating agent and the time and the labor required for the assurance of production conditions for a constant quality are unnecessary. Thus, the composition is useful also from the viewpoint of cost and productivity.

Pharmaceutical preparations containing the functional starch powder of the invention may have a coating for taste masking, damp proofing or the like. A coating agent is not particularly limited and includes, for example, cellulose type coating agents (e.g. ethyl cellulose, hydroxypropylmethyl cellulose phthalate, carboxymethylethyl cellulose, hydroxypropylmethyl cellulose acetate succinate, cellulose acetate succinate, cellulose acetate phthalate and cellulose acetate), acrylic polymer type coating agents (e.g. Eudragit RS, Eudragit L and Eudragit NE), shellac and silicone resins. These coating agents may be used alone or in combination. As a method for using these coating agents, a well-known method can be adopted. The coating agents may be dissolved in an organic solvent or suspended in water. A suspension of the coating agent in water may be granulated together with a pharmaceutically active ingredient(s) and other components.

The pharmaceutical preparations containing the functional starch powder of the invention include those which permit sustained release of an active ingredient(s) by diffusion from a gel layer formed from only the functional starch powder of the invention or a gel layer formed substantially from the functional starch powder of the invention used in combination with another release-sustaining base ingredient. These pharmaceutical preparations can be prepared by well-known methods such as mixing, stirring, granulation, particle size regulation, tabletting, etc. The phrase "formed substantially from the functional starch powder of the invention" means that the functional starch powder of the invention is incorporated into the pharmaceutical preparation in order to endow the pharmaceutical preparation with the various functions of the functional starch powder of the invention, such as a function of increasing the resistance to α-amylase, a function of enhancing the sustained-release capability and a function of assuring the sustained-release capability in a medium having a high ionic strength. For example, if formulation into a pharmaceutical form and the impartment of sustained-release properties can be achieved by the addition of the functional starch powder of the invention in a case where a release-sustaining base ingredient such as HPMC, methyl cellulose, HPC or the like is co-used which does not bring about a sufficient sustained-release effect under a high ionic strength, the achievement can be considered to be attributable to the effect of the functional starch powder of the invention.

The invention is illustrated in detail with the following examples, which should not be construed as limiting the scope of the invention. Methods for measuring physical properties in the examples and comparative examples are as follows.

(1) Volume Ratio

The term "volume ratio" is defined as $[b/a]^3$ when average particle sizes before and after swelling are taken as a (μm) and b (μm), respectively. The average particle size referred to here is calculated by summing up the maximum diameters "m" (μm) of individual particles observed under an optical microscope (magnification: 10, OPTIPHOT-POL mfd. by Nikon) and dividing the sum by the number "n" of particles subjected to the measurement (Σm/n). The average particle size is calculated for each of the following: starch particles before swelling and starch particles swollen by heating at 60 to 150° C.

(2) Water Retention Capacity (%)

$W_0$ (g) (about 1 g) of dried starch powder is placed in small portions in a 50-ml centrifuge tube containing about 15 ml of pure water and dispersed in the pure water while stirring until the dispersion becomes transparent or semitransparent. Pure water was added to fill the 50-ml centrifuge tube about 70% full therewith, followed by centrifugation (2000G, 10 minutes). After completion of the centrifugation, the separated upper layer is immediately discarded and then the water retention capacity is calculated from the weight W (g) of the residue as the lower layer (the total weight of starch and pure water retained by the starch) by the following equation:

$$\text{Water retention capacity}(\%) = 100 \times [W - W_0]/W_0$$

(3) Collapse Time (hr)

The term "collapse time" is defined as the disintegration time, in a test solution, of a cylindrical molded article with a diameter of 0.8 cm obtained by compressing 0.2 g of starch powder at 50 MPa. The test solution is the second solution (pH 6.8) described in the Japanese Pharmacopoeia (14th revision, p. 204) and a disintegration test is carried out by the use of an auxiliary plate according to the disintegration test method described in the Japanese Pharmacopoeia (14th revision).

(4) Gel Indentation Load (g)

The term "gel indentation load" is defined as a maximum load applied when a cylindrical adapter is pressed for 3 mm at a rate of 0.1 mm/sec with a rheometer (RHEONER, RE-33005, mfd. by YAMADEN) into a gel obtained by immersing, for 4 hours in pure water, a cylindrical molded article with a diameter of 1.13 cm obtained by compressing 0.5 g of starch powder at 50 MPa. The term "maximum load" means the following: when a gel layer is broken, the term means a maximum load value at the time of the breaking; and when the gel layer is not broken, the term means a maximum load value, which the adapter applies before it intrudes for 5 mm into the gelled cylindrical molded article. The maximum load is calculated as the average of five measurements.

(5) Amount (% By Weight) of Swollen or Dissolved Amylose and Amylopectin

The amount of swollen or dissolved amylose and amylopectin is determined by dispersing about 1 g of dried starch powder in 100 $cm^3$ of pure water, allowing the resulting dispersion to stand for 16 hours, calculating the volume of the upper layer portion of the dispersion separated into upper and lower layers and the weight percentage of solids in 30 $cm^3$ of the upper layer, and calculating the amount by the following equation:

$$\text{The amount (\% by weight) of swollen or dissolved} \\ \text{amylose and amylopectin} = \text{the volume } (cm^3) \text{ of} \\ \text{the upper layer portion} \div 30 \times \text{the weight } (g/cm^3) \text{ of} \\ \text{solids in 30 } cm^3 \text{ of the upper layer} \div \text{the dry} \\ \text{weight (g) of the starch powder} \times 100$$

(6) Particle Size (μm) of Starch Particles

The term "particle size of starch particles" is defined as the maximum diameter of a single particle when the starch particles are observed at a magnification of 200 to 1500 by the use of SEM (JEOL JSM-5510LV, mfd by JEOL LTD.; vapor deposition of Pt; JEOL JFC-1600 AUTO FINE COATER, mfd by JEOL LTD.). If single particles aggregate, then the diameter of the multi-particle aggregate is not considered in the particle size evaluation. However, even if particles are aggregated, their diameters can be considered as the particle size referred to when the boundary surfaces among the particles are clear and the maximum diameter of the single particle is clear because of, for example, the small size of the aggregated particles. The reason is that the maximum diameter of a single particle among them is precise.

(7) Degree of Swelling ($cm^3/g$)

Degree of swelling is determined by dispersing about 1 g of dried starch powder in 100 $cm^3$ of pure water, allowing the resulting dispersion to stand for 16 hours, and calculating the degree of swelling from the volume V of the lower layer portion of the dispersion separated into upper and lower layers, by the following equation:

Degree of swelling $(cm^3/g) = V(cm^3)/$ the dry weight (g) of the starch powder (8) Shell Structure As to the shell structure, 1 g of starch powder is dispersed in 100 cm³ of pure water and after standing for 16 hours, the lower layer portion of the dispersion separated into upper and lower layers is observed under an optical microscope (magnification: 10). In the case of the starch powder of the invention, the shell structure inherent in a starch raw material for the starch powder is completely present without loss thereof. On the other hand, in the case of pregelatinized starch, nothing is observed in the lower layer portion, or a flaky, massive or the like shell structure formed by the conversion of swollen or dissolved amylose and amylopectin to β-amylose and β-amylopectin is observed in the lower layer portion.

Example 1

A starch emulsion having a solid concentration of 5% was prepared by using potato starch as a starting material. The starch emulsion was gelatinized by heating at 95° C. for 45 minutes in a jacketed agitation vessel (4 L), diluted 2-fold with warm water at 60° C., and then continuously spray-dried at a flow rate of 8.3 L/hr while being maintained at 60° C., to obtain starch powder A. A cylindrical molded article with a diameter of 0.8 cm was obtained by compressing 0.2 g of prepared powder of acetaminophen (APAP)/starch powder A/crystalline cellulose "Ceolus" KG-802 (weight ratio: 10/60/30) at 60 MPa with a static-pressure press, and was subjected to a release-by-dissolution test. As test solutions, there were used solution I (pH 1.2), solution II (pH 6.8, ionic strength 0.14) and Mcilvaine solution (pH 7.2, ionic strength 0.39) described in the Japanese Pharmacopoeia. The test was carried out by adding α-amylase to each of these solutions to a concentration of 5 μm/cm³.

Table 1 shows the physical properties of starch powder A, and Table 2 shows the release-by-dissolution test result of the molded article of the prepared powder. The molded article containing starch powder A was not disintegrated in the test solutions even after the lapse of 8 hours. It had a sustained-release capability equal to that imparted by release-sustaining base ingredients which have been generally used. In addition, the molded article was free from pH dependence and the influence of ionic strength and moreover, had a good stability over a long period of time. Thus, it can be seen that the molded article is an excellent pharmaceutical preparation.

Example 2

Potato starch was packed in a stainless-steel vat (50 cm×25 cm) to a thickness of 5 cm, subjected to pressure reduction (600 mmHg) in a pressure container for 5 minutes, and then treated with compressed steam (120° C.) for 20 minutes. Using the treated potato starch as a starting material, a starch emulsion having a solid concentration of 5% was prepared. The starch emulsion was gelatinized by heating at 95° C. for 45 minutes in a jacketed agitation vessel (4 L), diluted 2-fold with warm water at 60° C., and then continuously spray-dried at a flow rate of 8.3 L/hr while being maintained at 60° C., to obtain starch powder B. A cylindrical molded article with a diameter of 0.8 cm was obtained by compressing 0.2 g of prepared powder of acetaminophen (APAP)/starch powder B/crystalline cellulose "Ceolus" KG-802 (weight ratio: 10/60/30) at 60 MPa with a static-pressure press, and was subjected to a release-by-dissolution test. As test solutions, solution I (pH 1.2), solution II (pH 6.8, ionic strength 0.14) and Mcilvaine solution (pH 7.2, ionic strength 0.39) were used as described in the Japanese Pharmacopoeia. The test was carried out by adding α-amylase to each of these solutions to a concentration of 5 μm/cm³.

Table 1 shows the physical properties of starch powder B, Table 2 shows the release-by-dissolution test result of the molded article of the prepared powder, and FIG. 1 shows an electron micrograph (600 magnifications) of starch powder B. Table 3 shows the result of subjecting the cylindrical molded article to a release-by-dissolution test in the same manner as above after storing the cylindrical molded article in a sealed-in state at 40° C. and 75% RH for 2 weeks. The molded article containing starch powder B was not disintegrated in the test solutions even after the lapse of 8 hours. It had a sustained-release capability equal to that imparted by release-sustaining base ingredients that have been generally used. In addition, the molded article was free from pH dependence and the influence of ionic strength and moreover, had a good stability over a long period of time. Thus, it can be seen that the molded article is an excellent pharmaceutical preparation.

Example 3

Potato starch was packed in a stainless-steel vat (50 cm×25 cm) to a thickness of 5 cm, subjected to pressure reduction (600 mmHg) in a pressure container for 5 minutes, and then treated with compressed steam (120° C.) for 20 minutes. Using the treated potato starch as a starting material, a starch emulsion having a solid concentration of 5% was prepared. The starch emulsion was gelatinized (outlet temperature: 105° C.) by heating at 20 L/hr in a jet cooker, continuously passed through a residence tube (85° C.) with a capacity of 3 L, and then spray-dried to obtain starch powder C. The residence time was 9 minutes.

A release-by-dissolution test on a molded article of prepared powder was carried out by the same procedure as in Example 1 except for using starch powder C. Table 1 shows the physical properties of starch powder C and Table 2 shows the release-by-dissolution test result of the molded article of prepared powder. The molded article containing starch powder C was not disintegrated in the test solutions even after the lapse of 8 hours. It had a sustained-release capability equal to that imparted by release-sustaining base ingredients that have been generally used. In addition, the molded article was free from pH dependence and the influence of ionic strength. Thus, it can be seen that the molded article is an excellent pharmaceutical preparation.

Example 4

Potato starch was packed in a stainless-steel vat (50 cm×25 cm) to a thickness of 5 cm, subjected to pressure reduction (600 mmHg) in a pressure container for 5 minutes, and then treated with compressed steam (120° C.) for 20 minutes. Using the treated potato starch as a starting material, a starch emulsion having a solid concentration of 5% was prepared. The starch emulsion was gelatinized (outlet temperature:

120° C.) by heating at 20 L/hr in a jet cooker, continuously passed through a residence tube (120° C.) with a capacity of 3 L, and then spray-dried to obtain starch powder D. The residence time was 9 minutes.

A release-by-dissolution test on a molded article of prepared powder was carried out by the same procedure as in Example 1 except for using starch powder D. Table 1 shows the physical properties of starch powder D, and Table 2 shows the release-by-dissolution test result of the molded article of prepared powder. The molded article containing starch powder D was not disintegrated in the test solutions even after the lapse of 8 hours. It had a sustained-release capability equal to that imparted by release-sustaining base ingredients that have been generally used. In addition, the molded article was free from pH dependence and the influence of ionic strength. Thus, it can be seen that the molded article is an excellent pharmaceutical preparation.

Example 5

Potato starch was packed in a stainless steel vat (50 cm×25 cm) to a thickness of 5 cm, subjected to pressure reduction (600 mmHg) in a pressure container for 5 minutes, and then treated with compressed steam (130° C.) for 20 minutes. Using the treated potato starch as a starting material, a starch emulsion having a solid concentration of 5% was prepared. The starch emulsion was gelatinized (outlet temperature: 115° C.) by heating at 20 L/hr in a jet cooker, and then spray-dried to obtain starch powder E.

A release-by-dissolution test on a molded article of prepared powder was carried out by the same procedure as in Example 1 except for using starch powder E. Table 1 shows the physical properties of the starch powder and Table 2 shows the release-by-dissolution test result of the molded article of prepared powder. The molded article containing starch powder E was not disintegrated in the test solutions even after the lapse of 8 hours. It had a sustained-release capability equal to that imparted by release-sustaining base ingredients that have been generally used. In addition, the molded article was free from pH dependence and the influence of ionic strength. Thus, it can be seen that the molded article is an excellent pharmaceutical preparation.

Example 6

Potato starch was packed in a stainless-steel vat (50 cm×25 cm) to a thickness of 5 cm, subjected to pressure reduction (600 mmHg) in a pressure container for 5 minutes, and then treated with compressed steam (120° C.) for 20 minutes. Using the treated potato starch as a starting material, a starch emulsion having a solid concentration of 5% was prepared. The starch emulsion was gelatinized (outlet temperature: 100° C.) by heating at 20 L/hr in a jet cooker, continuously passed through a residence tube (100° C.) with a capacity of 3 L, and then spray-dried to obtain starch powder F. The residence time was 9 minutes.

In an agitation granulator (Vertical Granulator FM-VG-10, mfd. by Powrex Co.) 15 g of starch powder F, 1120 g of 200M lactose (Pharmatose 200M, mfd. by DMV International) and 480 g of official corn starch (mfd. by Nippon Starch Chemical Co., Ltd.) were placed and premixed for 3 minutes under conditions of a blade revolution rate of 280 rpm and a cross-screw revolution rate of 3000 rpm. Then, 400 g of pure water was added all at once as binding water, followed by granulation for 3 minutes under conditions of a blade revolution rate of 280 rpm and a cross-screw revolution rate of 3000 rpm. The resulting granulation product was dried on trays at 60° C. for 16 hours and then sifted through a screen having a screen opening of 1410 μm, and granules that could pass through the screen were used as granules A for tabletting. To granules A for tabletting was added magnesium stearate in an amount of 0.5% by weight based on the weight of the resulting mixture, and the mixture was compressed into tablets at a compression pressure of 5 kN, 10 kN or 15 kN with a rotary tabletting machine (Clean Press, correct 12HUK, mfd. by Kikusui Seisakusho Ltd.) under the following conditions: 54 rpm, attachment of a Φ8 mm-12R pestle, and open feed.

Figure 2:
FIG. 2 An electron micrograph (600 magnifications) of starch powder F prepared in Example 6.
Figure 9:
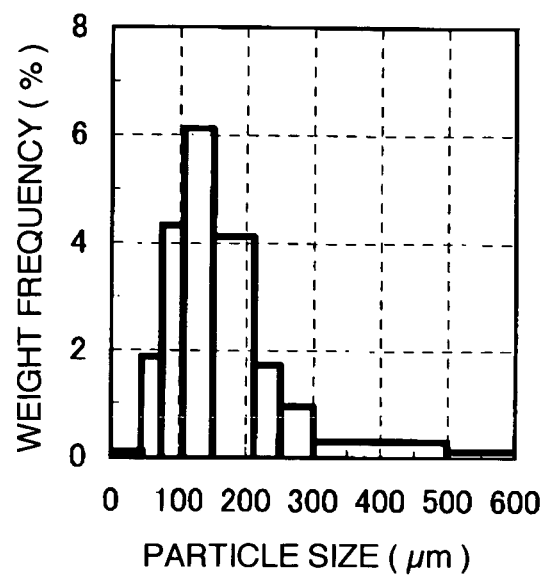
FIG. 9 A graph showing the particle size distribution of granules A for tabletting produced from starch powder F in Example 6.

Table 1 shows the physical properties of starch powder F and FIG. 2 shows an electron micrograph (600 magnifications) of starch powder F. FIG. 9 shows the particle size distribution of granules A for tabletting and Table 4 shows physical properties of the tablets obtained. Granules A for tabletting produced by adding starch powder F in the form of powder showed the sharp particle size distribution and the tablets produced from granules A for tabletting had a high hardness and excellent disintegrating properties.

The weight frequency (%) in FIG. 9 is explained below. Using IS screens having screen openings of 45, 75, 106, 150, 212, 250, 300, 500 and 710 μm, respectively, 10 g of the granules for tabletting are sieved with a low-tap screen classifier for 10 minutes, and the weight percentage of granules remaining on each screen is calculated and converted to a weight frequency (at intervals of 10 μm) in each of the above screen opening ranges. For example, when the weight percentage of granules for tabletting in the screen opening range of 45 μm to 75 μm is a (%), the weight frequency b is calculated to be [a/(75−45)]×10(%) by conversion. The same applies to FIGS. 10 to 12 described hereinafter.

Example 7

Placed in a vessel was 500 g of pure water, and 40 g of starch powder E of Example 5 was added in small portions while stirring at 5000 rpm in a TK homomixer (Model MARKII, mfd. by Tokushu Kika Kogyo Co., Ltd.). After the whole amount of starch powder E was added, the resulting mixture was stirred for 30 minutes to obtain a homogeneous suspension of starch powder E. In an agitation granulator (Vertical Granulator FM-VG-10, mfd. by Powrex Co.) were placed 1120 g of 200M lactose (Pharmatose 200M, mfd. by DMV International) and 480 g of official corn starch (mfd. by Nippon Starch Chemical Co., Ltd.), and premixed for 3 minutes under conditions of a blade revolution rate of 280 rpm and a cross-screw revolution rate of 3000 rpm. Then, 400 g of the homogeneous suspension of starch powder E obtained above was added all at once as a binder, followed by granulation for 3 minutes under conditions of a blade revolution rate of 280 rpm and a cross-screw revolution rate of 3000 rpm. The granulation product obtained was dried on trays at 60° C. for 16 hours and then sifted through a screen having a screen opening of 1410 μm, and granules that could pass through the screen were used as granules B for tabletting. To granules B for tabletting was added magnesium stearate in an amount of 0.5% by weight based on the weight of the resulting mixture, and the mixture was compressed into tablets at a compression pressure of 5 kN, 10 kN or 15 kN with a rotary tabletting machine (Clean Press, correct 12HUK, mfd. by Kikusui Seisakusho Ltd.) under the following conditions: 54 rpm, attachment of a Φ8 mm-12R pestle, and open feed.

Figure 11:
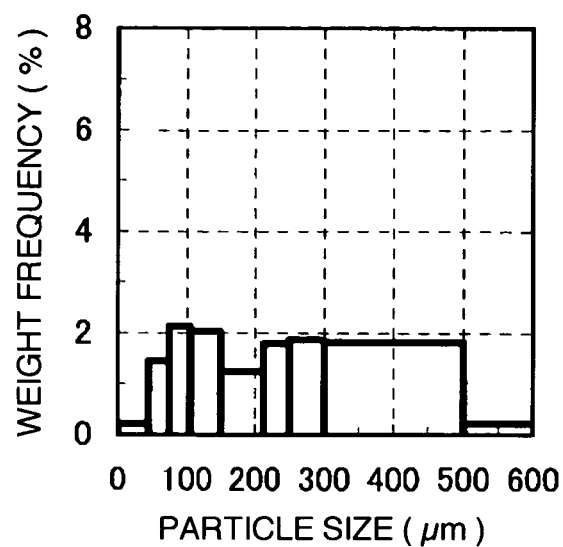
FIG. 11 A graph showing the particle size distribution of granules C for tabletting produced from commercial hydroxypropyl cellulose (HPC-L) in Comparative Example 9.

FIG. 11 shows the particle size distribution of granules B for tabletting and Table 4 shows physical properties of the tablets obtained. Granules B for tabletting produced by adding starch powder E in the form of the suspension showed the sharp particle size distribution and the tablets produced from granules B for tabletting had a high hardness and excellent disintegrating properties.

Comparative Example 1

Figure 3:
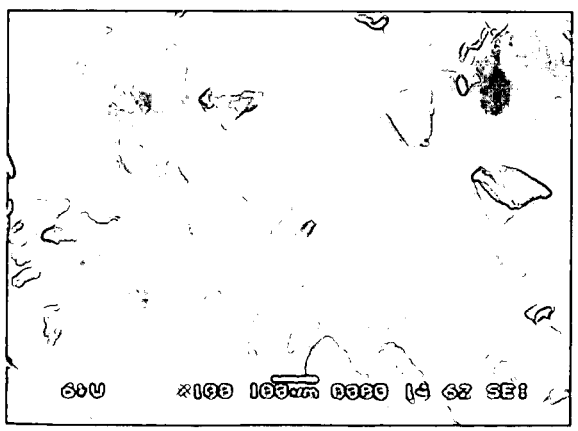
FIG. 3 An electron micrograph (100 magnifications) of the commercial potato pregelatinized starch used in Comparative Example 1.

A release-by-dissolution test on a molded article of prepared powder was carried out by the same procedure as in Example 1 except for using commercial potato pregelatinized starch (Matsunorin M, mfd. by Matsutani Chemical Industry Co., Ltd.) in place of starch powder A. Table 1 shows the physical properties of the commercial potato pregelatinized starch, FIG. 3 shows an electron micrograph (100 magnifications) of this pregelatinized starch, and Table 2 shows the release-by-dissolution test result of the molded article of prepared powder.

The commercial potato pregelatinized starch had a collapse time of 5 hr or more and a sufficient water retention capacity, but it could not have a sufficient release-sustaining capability because of its low gel indentation load and because it exhibited no release-sustaining capability at a high pH or a high ionic strength.

Comparative Example 2

Figure 4:
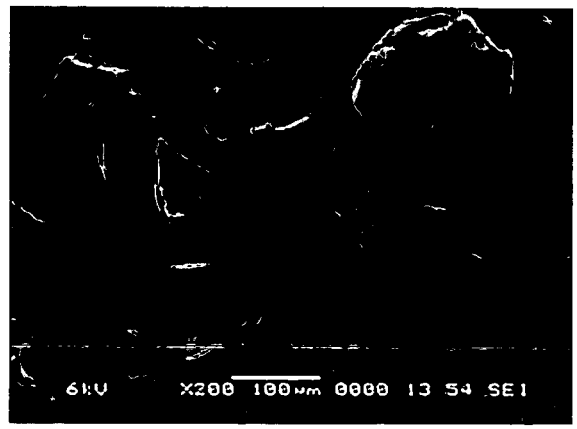
FIG. 4 An electron micrograph (200 magnifications) of the commercial corn pregelatinized starch used in Comparative Example 2.

A release-by-dissolution test on a molded article of prepared powder was carried out by the same procedure as in Example 1 except for using commercial corn pregelatinized starch (mfd. by Sanwa Cornstarch Co., Ltd.) in place of starch powder A. Table 1 shows the physical properties of the commercial corn pregelatinized starch, FIG. 4 shows an electron micrograph (200 magnifications) of this pregelatinized starch, and Table 2 shows the release-by-dissolution test result of the molded article of prepared powder.

The commercial corn pregelatinized starch had a collapse time of less than 5 hr and a sufficient water retention capacity but it had substantially no release-sustaining capability because of its low gel indentation load.

Comparative Example 3

Figure 5:
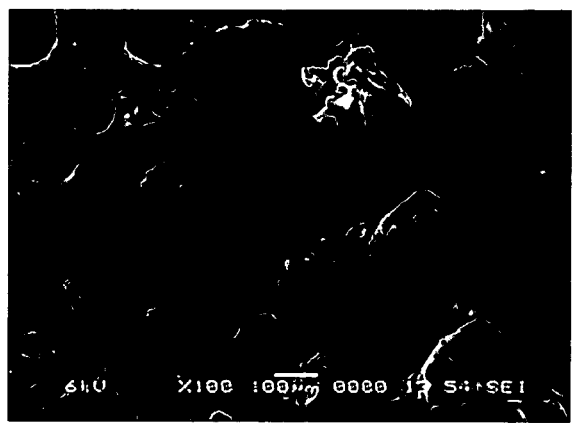
FIG. 5 An electron micrograph (100 magnifications) of the commercial high-amylose corn pregelatinized starch used in Comparative Example 3.

A release-by-dissolution test on a molded article of prepared powder was carried out by the same procedure as in Example 1 except for using commercial high-amylose corn pregelatinized starch (mfd. by Sanwa Cornstarch Co., Ltd.) in place of starch powder A. Table 1 shows the physical properties of the commercial high-amylose corn pregelatinized starch, FIG. 5 shows an electron micrograph (100 magnifications) of this pregelatinized starch, and Table 2 shows the release-by-dissolution test result of the molded article of prepared powder.

The commercial high-amylose corn pregelatinized starch had a collapse time of 5 hr or less and an insufficient water retention capacity and exhibited no release-sustaining properties at all.

Comparative Example 4

Figure 6:
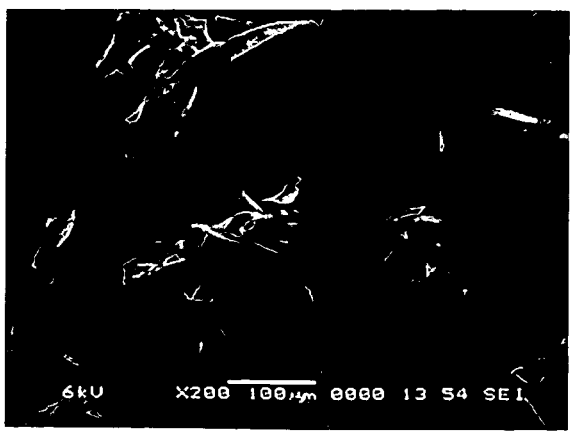
FIG. 6 An electron micrograph (200 magnifications) of the commercial waxy corn pregelatinized starch used in Comparative Example 4.

A release-by-dissolution test on a molded article of prepared powder was carried out by the same procedure as in Example 1 except for using commercial waxy corn pregelatinized starch (mfd. by Sanwa Cornstarch Co., Ltd.) in place of starch powder A. Table 1 shows the physical properties of the commercial waxy corn pregelatinized starch, FIG. 6 shows an electron micrograph (200 magnifications) of this pregelatinized starch, and Table 2 shows the release-by-dissolution test result of the molded article of prepared powder.

The commercial waxy corn pregelatinized starch had a sufficient water retention capacity but it had a collapse time of 5 hr or less and exhibited no release-sustaining properties at all.

Comparative Example 5

Figure 7:
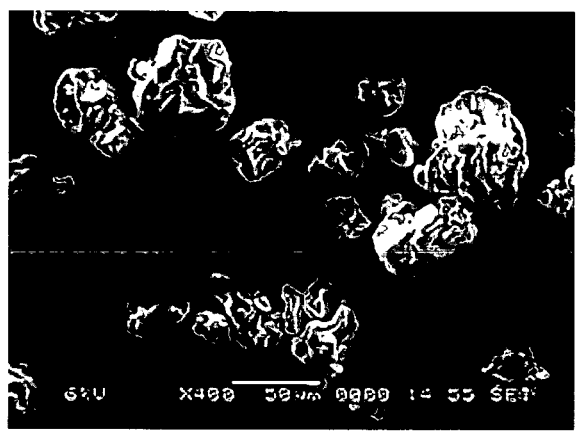
FIG. 7 An electron micrograph (400 magnifications) of the commercial partly pregelatinized starch (PCS) used in Comparative Example 5.

A release-by-dissolution test on a molded article of prepared powder was carried out by the same procedure as in Example 1 except for using commercial partly pregelatinized starch (PCS, mfd. by Sanwa Cornstarch Co., Ltd.) in place of starch powder A. Table 1 shows the physical properties of PCS, FIG. 7 shows an electron micrograph (400 magnifications) of PCS, and Table 2 shows the release-by-dissolution test result of the molded article of prepared powder.

PCS had a sufficient water retention capacity but it had a collapse time of 5 hr or less and exhibited no release-sustaining properties at all.

Comparative Example 6

A release-by-dissolution test on a molded article of prepared powder was carried out by the same procedure as in Example 1 except for using commercial partly pregelatinized starch (Starch 1500) in place of starch powder A. Table 1 shows the physical properties of Starch 1500 and Table 2 shows the release-by-dissolution test result of the molded article of prepared powder.

Starch 1500 had an insufficient water retention capacity and a collapse time of 5 hr or less and exhibited no release-sustaining properties at all.

Comparative Example 7

A release-by-dissolution test on a molded article of prepared powder was carried out by the same procedure as in Example 1 except for using a commercial release-sustaining base ingredient of non-starch type (HPMC 60SH, mfd. by Shin-Etsu Chemical Co., Ltd.) in place of starch powder A. Table 1 shows the physical properties of HPMC 60SH and Table 2 shows the release-by-dissolution test result of the molded article of prepared powder.

HPMC 60SH was sufficient in collapse time, gel indentation load, water retention capacity and release-sustaining capability and desirably had no pH dependence. But it was found that at a high ionic strength, HPMC 60SH becomes unable to be sufficiently hydrated, and exhibited no release-sustaining properties at all.

Comparative Example 8

Official corn starch was made into a 3% by weight slurry and the slurry was completely gelatinized by heating at 90° C. and sprayed into an atmosphere of an inlet temperature of 180° C. and an outlet temperature of 90° C. at a slurry feed rate of 5 L/hr with a spray dryer having a two-fluid nozzle, to obtain starch powder G. A release-by-dissolution test on a molded article of prepared powder was carried out by the same procedure as in Example 1 except for using starch powder G in place of starch powder A.

Figure 8:
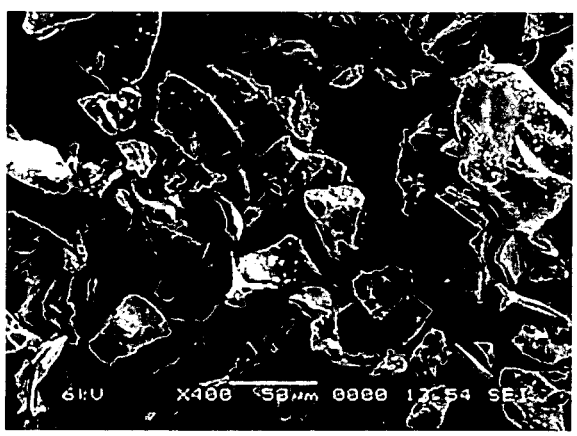
FIG. 8 An electron micrograph (400 magnifications) of starch powder G prepared in Comparative Example 8.

Table 1 shows the physical properties of starch powder G, FIG. 8 shows an electron micrograph (400 magnifications) of starch powder G, and Table 2 shows the release-by-dissolution test result of the molded article of prepared powder. Starch powder G had an insufficient water retention capacity and a collapse time of 5 hr or less and exhibited no release-sustaining properties at all.

Comparative Example 9

Figure 10:
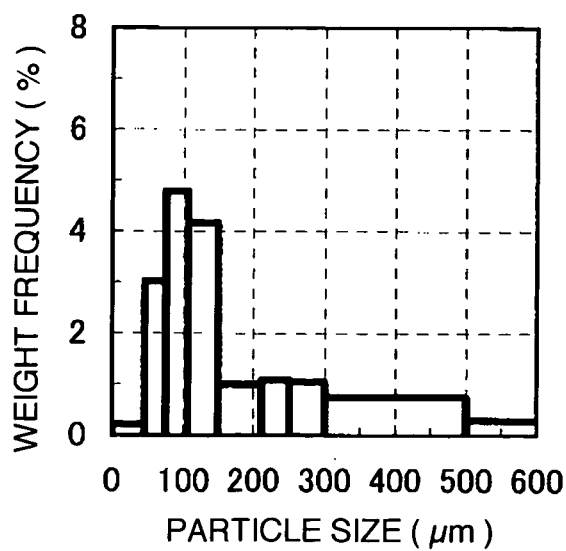
FIG. 10 A graph showing the particle size distribution of granules B for tabletting produced from a suspension of starch powder D in Example 7.

Granules C for tabletting were obtained by the same procedure as in Example 6 except for using 48 g of commercial hydroxypropyl cellulose (HPC-L, mfd. by Nippon Soda Co., Ltd.) in place of 15 g of starch powder F. Tablets were produced by the same procedure as in Example 6 except for using granules C for tabletting. FIG. 10 shows the particle size distribution of granules C for tabletting and Table 4 shows physical properties of the tablets obtained.

Granules C for tabletting produced by adding HPC-L in the form of powder had the broad particle size distribution, and the tablets produced from granules C for tabletting had a lower hardness and a longer disintegration time than did the tablets produced from granules A for tabletting in Example 6.

Comparative Example 10

Figure 12:
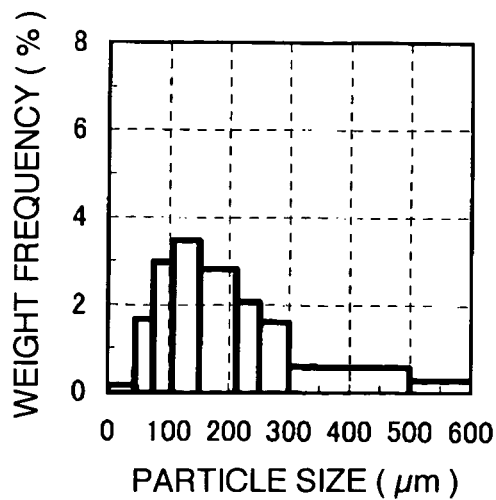
FIG. 12 A graph showing the particle size distribution of granules D for tabletting produced from commercial hydroxypropyl cellulose (HPC-L) in Comparative Example 10.

Granules D for tabletting were obtained by the same procedure as in Example 7 except for using commercial hydroxypropyl cellulose (HPC-L, mfd. by Nippon Soda Co., Ltd.) in place of starch powder E. Tablets were produced by the same procedure as in Example 7 except for using granules D for tabletting. FIG. 12 shows the particle size distribution of granules D for tabletting and Table 4 shows physical properties of the tablets obtained.

Granules D for tabletting produced by adding HPC-L in the form of a solution had the sharp particle size distribution, but the tablets produced from granules D for tabletting had a lower hardness and a longer disintegration time than did the tablets produced from granules B for tabletting in Example 7.

TABLE 1

| Sample | Volume ratio | Particle size of starch particles having an indent(s) (μm) | Water retention capacity (%) | Collapse time (hr) | Gel indentation load (g) | Amount of swollen or dissolved amylose and amylopectin (%) | Degree of swelling (cm³/g) | Shell structure |
|---|---|---|---|---|---|---|---|---|
| Example 1 | 25 | 140 | 950 | >8 | 900 | 45 | 30 | Yes |
| Example 2 | 32 | 140 | 1435 | >8 | 1100 | 43 | 33 | Yes |
| Example 3 | 94 | 200 | 1383 | >8 | 700 | 48 | 29 | Yes |
| Example 4 | 40 | 150 | 738 | >8 | ≥2000 | 72 | 5 | Yes |
| Example 5 | 94 | 200 | 532 | >8 | 311 | 64 | 1 | Yes |
| Example 6 | 317 | 300 | 1474 | >8 | 229 | 16 | 30 | Yes |
| Comparative Example 1 | Not measurable owing to dissolution | — (No indent) | 606 | 7 | 130 | 91 | 2 | No |
| Comparative Example 2 | Not measurable owing to dissolution | — (No indent) | 1284 | 4.5 | 75 | 19 | 19 | No (flanky) |
| Comparative Example 3 | Not measurable owing to dissolution | — (No indent) | 364 | 0.8 | Not measurable | 22 | 5 | No (massive) |
| Comparative Example 4 | Not measurable owing to dissolution | — (No indent) | 1046 | 2.8 | Not measurable | 57 | 15.5 | No |
| Comparative Example 5 | 8 | 20 | 511 | 0.5 | Not measurable | 2 | 8.6 | Yes |
| Comparative Example 6 | 9 | 20 | 356 | 0.3 | Not measurable | 11 | 9 | Yes |
| Comparative Example 7 | — (Non-starch particles) | — (Non-starch particles) | 682 | >8 | ≥2000 | — (Non-starch particles) | 0 (Dissolution) | — (Non-starch particles) |
| Comparative | Not | — | 340 | 3 | 60 | 32 | 16 | No |

TABLE 1-continued

| Sample | Volume ratio | Particle size of starch particles having an indent(s) (μm) | Water retention capacity (%) | Collapse time (hr) | Gel indentation load (g) | Amount of swollen or dissolved amylose and amylopectin (%) | Degree of swelling (cm³/g) | Shell structure |
|---|---|---|---|---|---|---|---|---|
| Example 8 | measurable owing to dissolution | (No indent) | | | | | | |

TABLE 2

| | APAP release-by-dissolution rate after 2 hr (%) | | | APAP release-by-dissolution rate after 5 h (%) | | |
|---|---|---|---|---|---|---|
| Sample | Solution I•α-amylase | Solution II•α-amylase | Mcilvaine•α-amylase | Solution I•α-amylase | Solution II•α-amylase | Mcilvaine•α-amylase |
| Example 1 | 40 | 40 | 35 | 68 | 71 | 65 |
| Example 2 | 39 | 39 | 33 | 66 | 70 | 62 |
| Example 3 | 38 | 38 | 32 | 65 | 73 | 65 |
| Example 4 | 38 | 46 | 43 | 61 | 71 | 65 |
| Example 5 | 40 | 40 | 40 | 66 | 70 | 65 |
| Comparative Example 1 | 35 | 64 | 100 | 60 | 94 | 100 |
| Comparative Example 2 | 81 | 81 | 100 | 90 | 100 | 100 |
| Comparative Example 3 | 100 | 100 | 100 | 100 | 100 | 100 |
| Comparative Example 4 | 100 | 100 | 100 | 100 | 100 | 100 |
| Comparative Example 5 | 100 | 100 | 100 | 100 | 100 | 100 |
| Comparative Example 6 | 100 | 100 | 100 | 100 | 100 | 100 |
| Comparative Example 7 | 39 | 41 | 100 | 73 | 70 | 100 |
| Comparative Example 8 | 90 | 90 | 100 | 100 | 100 | 100 |

TABLE 3

| | APAP release-by-dissolution rate at the beginning (%) | | APAP release-by-dissolution rate after standing for 2 weeks (%) | |
|---|---|---|---|---|
| Sample | Solution II•α-amylase 2 hr after | Solution II•α-amylase 5 hr after | Solution II•α-amylase 2 hr after | Solution II•α-amylase 5 hr after |
| Example 2 | 39 | 70 | 42 | 70 |

INDUSTRIAL APPLICABILITY

The functional starch powder of the present invention has a high resistance to α-amylase, a high resistance to ionic strength and a sufficient release-sustaining capability. Therefore, the functional starch powder is used in medicines, agrochemicals, fertilizers, feed, food, industry, cosmetics, etc. in the form of a composition comprising the functional starch powder and one or more active ingredients selected from pharmaceutically active ingredients, agrochemical ingredients, ingredients for fertilizer, ingredients for feed, ingredients for food, ingredients for cosmetic, coloring maters, fla-

TABLE 4

| | Striking pressure 5 kN | | Striking pressure 10 kN | | Striking pressure 15 kN | |
|---|---|---|---|---|---|---|
| | Tablet hardness (N) | Disintegration time (s) | Tablet hardness (N) | Disintegration time (s) | Tablet hardness (N) | Disintegration time (s) |
| Example 6 | 21 | 18 | 60 | 20 | 107 | 29 |
| Example 7 | 16 | 18 | 50 | 26 | 96 | 39 |
| Comparative Example 9 | 11 | 183 | 44 | 185 | 64 | 218 |
| Comparative Example 10 | 8 | 171 | 40 | 198 | 72 | 221 | voring materials, metals, ceramics, catalysts and surfactants, which composition permits control of the release of the active ingredient(s).

The invention claimed is:

1. A method for producing functional starch powder, which comprises:

subjecting a potato starch to a pressure reduction to 600 mm Hg and then heat treating the potato starch to a temperature of 100 to 130° C. using compressed steam at a temperature of at least 120° C., heating the potato starch in the presence of 40% by weight or more water at 60 to 150° C. to swell starch particles of the potato starch, and subsequently drying the swollen potato starch particles to obtain a powder mixture comprising the potato starch particles and amylose and amylopectin present on the exteriors of these potato starch particles, wherein the functional potato starch powder has a water retention capacity of 400% or more, a collapse time of 5 hr or more, and a gel indentation load of 200 g or more, 10% or more of all functional potato starch powder particles observable in the field of vision at a magnification of 600 are potato starch particles with a particle size of 50 to 500 μm, the potato starch particles have a structure indented in one or more parts, and 10 to 90% by weight of the total amylose and amylopectin in the functional potato starch powder is present on the exteriors of the starch particles.

2. The method for producing functional starch powder according to claim 1, wherein some or all of starch particles of the potato starch are swollen at a volume ratio of 10 or more.

3. The method for producing functional starch powder according to claim 2, wherein the volume ratio at which the some or all of starch particles of the potato starch are swollen is 400 or less.

* * * * *